Feb. 24, 1959 | E. G. FISHER | Plant Pat. 1,812
ROSE PLANT
Filed July 16, 1958
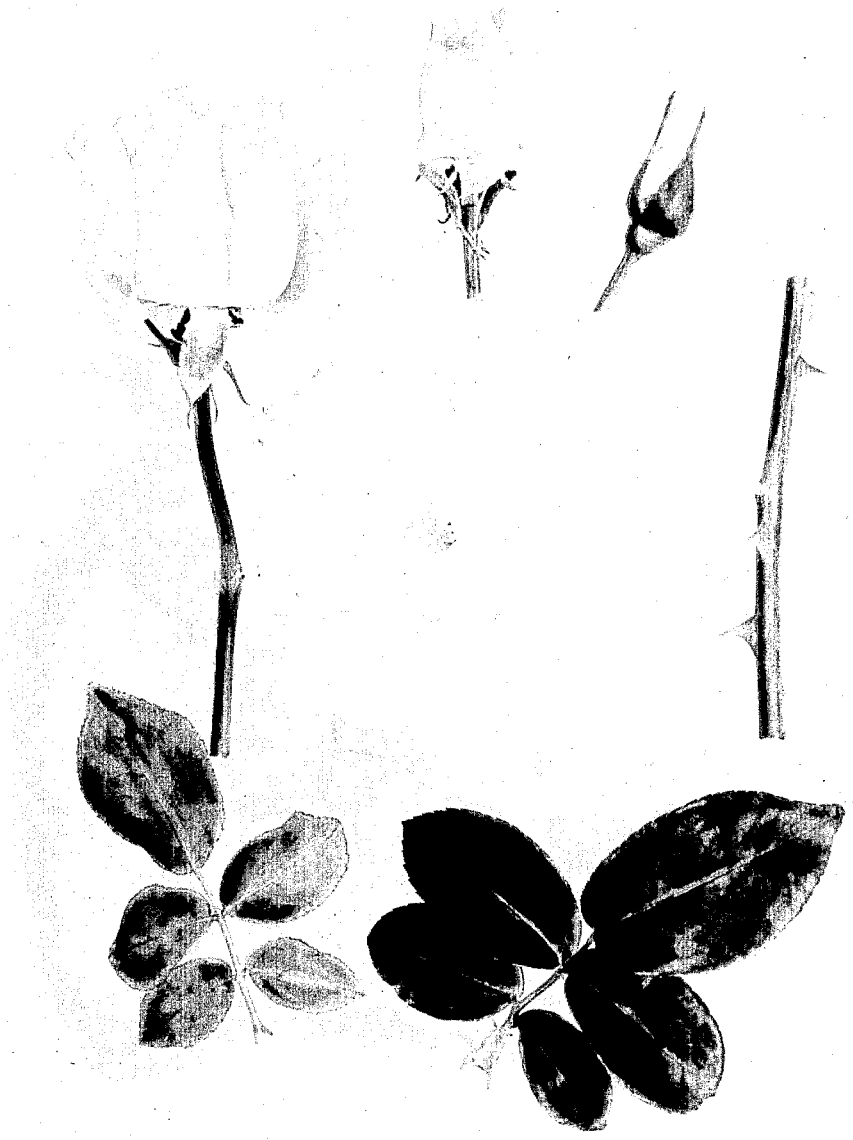
ESTHER GLADYS FISHER
Inventor
Shumaker & Mathis
Attorneys United States Patent Office Plant Pat. 1,812

Patented Feb. 24, 1959

1,812

ROSE PLANT

Esther Gladys Fisher, Woburn, Mass., assignor to The Conard-Pyle Company, West Grove, Pa., a corporation of Pennsylvania Application July 16, 1958, Serial No. 749,039

1 Claim. (Cl. 47—61)

The present invention relates to a new and distinct clonal variety of rose plant of the hybrid tea class produced by crossing Peace (Plant Patent No. 591) with Mission Bells (Plant Patent No. 923).

The primary objectives of this breeding were to produce a new rose variety combining the vigorous, heavy growth, the excellent foliage and the very double bloom characteristics of Peace, with the pink color tones, bud form and freedom of bloom of Mission Bells. I desired also to project into the seedlings of this breeding the recessive red color tones known to be present in the chromosomes of Peace as a result of its parentage, as well as the desirable bloom characteristics from the McGredy strain present in its progenitors.

That several of these objectives were achieved is evidenced by the following characteristics which, in combination, are unique and distinguish the variety from its parents and other varieties in commerce:

1. The Fire Red coloration of the wide open bloom which is overlaid with Spiraea Red and shows amber yellow at the center.
2. The glossy dark green, abundant foliage.
3. The strong, stocky habit of growth.
4. The large and well formed blooms which show a wide range of color variation, dependent on temperatures, soils and differing degrees of maturity, combining shades and tints of rich red and yellow color tones in varying proportions.

Asexual reproduction of my new variety by budding as performed at West Grove, Pennsylvania, shows that the aforementioned characteristics are established and transmitted through succeeding propagations.

The accompanying drawing shows typical specimens of the vegetative growth and flowers of my new variety depicted in color as nearly true as it is reasonably possible to make the same in a color illustration of this character.

The following is a detailed description of my new variety, with color terminology in accordance with the Horticultural Color Chart of the British Color Council:

Type: Hardy; bush; outdoor; seedling; for cut flowers and for garden decoration.
Class: Hybrid tea.
Breeding: Seedling.
*Seed parent.*—Peace (Plant Patent No. 591).
*Pollen parent.*—Mission Bells (Plant Patent No. 923).

*Flower*

Locality where grown: West Grove, Pennsylvania.
Flowers borne: Singly, on normal medium stems.
Quantity of bloom: Free outdoors.
Continuity: Continuous.
Fragrance: Penetrating spicy.
Bud:
*Peduncle.*—Medium long; medium heavy; erect; Fern Green 0862/1 overlaid with Garnet Brown 00918/3; smooth.

*Before calyx breaks.* — Size — medium. Form — pointed ovoid with foliaceous appendages on the surface of the bud; with slender bristle-like foliaceous parts extending beyond the tip of the bud equal to ¼ or more of its length.
*As calyx breaks.* — Color — Currant Red 821/2 spotted with Citron Yellow 763.
*As first petal opens.*—Size—medium. Form—pointed ovoid. Color: outside—Jasper Red 018 blotched here and there on the midrib with Spiraea Red 025; base of petal Citron Green 763/1; inside—Fire Red 15/1 lightly streaked with Blood Red 820/2. Center of petal is usually blotched and streaked with Phlox Pink 625. These colors grade into Carrot Red 612 which in turn grades to Aureolin 3. Opening—opens up well.

Bloom:
*Size when fully open.*—Large, 4½ inches to 6 inches.
*Petalage.*—Double, from 35 to 40 petals; arranged regularly.
*Form.*—High centered at first; becoming cupped; petals remaining at first loosely rolled outward; becoming later at maturity very loosely rolled outward.

Petals: Leathery; with inside and outside satiny. Shape: outer—roundly ovate with 1 notch; intermediate—roundly ovate with 1 notch; inner—ovate, irregular.

This description of a newly opened flower was made from a rose grown outdoors in August, 1957, at West Grove, Pennsylvania.

*Color.*—Outer petal: outside surface—Spinel Red 0023/1 overlaid with Spiraea Red 025/1 where first exposed to sun; base of petal Dresden Yellow 64; inside surface—Solferino Purple 26/1 with basal quarter of petal Mimosa Yellow 602. Intermediate petal: outside surface—Salmon 412/1 grading to Chrome Yellow 605/1 veined with Azalea Pink 618/1; basal quarter of petal Mimosa Yellow 602/1; inside surface—Straw Yellow 604/2 with basal quarter Mimosa Yellow 602. Inner petal: outside surface—Maize Yellow 607/1 suffused with Nasturtium Orange 610/1, grading to Mimosa Yellow 602/1 over basal quarter of petal; inside surface—Straw Yellow 604/1 with basal quarter Aureolin 3/1.

This description was made from a rose that was open for three days outdoors in September, 1957, at West Groove, Pennsylvania.

*Color.*—Outer petal: outside surface—Fire Red 15/3 lightly overlaid with Spiraea Red 025/1 and where first exposed to sun heavily overlaid with Spiraea Red 025; base of petal Indian Yellow 6/2; inside surface — Fire Red 15/3 washed with Spiraea Red 025/1 grading to Indian Yellow 6/2 lightly overlaid with Spiraea Red 025/2; base of petal Lemon Yellow 4. Inner petal: outside surface—intermediate between Azalea Pink 618/1 and 618/2 grading to Aureolin 3/2 over basal quarter of petal; inside surface—Azalea Pink 618/3 at outer margin, grading to Amber Yellow 505/2 and to Aureolin 3/2 at base of petal. General color effect: newly opened flower—Straw Yellow 604/1, outer petals edged with Solferino Purple 26/1; three days open—Fire Red 15/3 overlaid with Spiraea Red 025/1 at outer margin of petals, with center of bloom Amber Yellow 505/2.
*Behavior.*—Drop off cleanly; fading purple; effected by cold, wet weather as follows: Spiraea Red coloration less prominent.

*Flower longevity.*—3 days in September; cut roses grown outdoors kept at living room temperatures 4 days in September.

*Reproductive organs*

Stamens: Many; arranged regularly about pistils.
Filaments: Many; most with anthers; medium length. Color—Blood Red 820/1 with base Lemon Yellow 4.
Anthers: All open at once; medium. Color—Barium Yellow 503. Occasionally an anther fused with a petaloid.
Pollen: Moderate; gold.
Pistils: Medium.
Styles: Uneven; short; medium; bunched.
Stigma: Pink.
Ovaries: All enclosed in receptacle.
Hips: None observed.
Sepals: Permanent; moderately long; straight spear shaped.
Seeds: None observed.

*Plant*

Foliage:

*Leaves.*—Compound of 5 leaflets; normal; medium; moderately heavy glossy.

*Leaflets.*—Shape—oval with apex acute, margin simply serrate.

*Color.* — Mature: upper surface — Spinach Green 0960; under surface—Spinach Green 0960/2. Young: upper surface—Fern Green 0862 lightly overlaid with Maroon 1030; under surface—Erythrite Red 0027.

*Rachis (the supporting stem of the compound leaf.* — Medium. Upper side — grooved hairy. Under side—smooth.

*Stipules.*—Medium; moderately narrow; with short points; turning out at an angle of more than 45°.

*Disease.*—Resistance comparable to the average variety growing under the same cultural conditions.

Growth:

*Habit.*—Bushy; much branched.

*Growth.*—Moderate free.

*Canes.*—Medium.

*Main stems.*—Dull; color—Spinach Green 0960/1. Prickles—several; color—Garnet Brown 00918/2. Hairs—none.

*Branches.* — Color — Spinach Green 0960/1. Prickles—color—Garnet Brown 00918/2 at base with point underlaid with Straw Yellow 604. Hairs—none.

I claim:

A new and distinct variety of rose plant of the hybrid tea class, substantially as herein shown and described, characterized particularly as to novelty by the Fire Red overlaid with Spiraea Red coloration of the open blooms, changing to Amber Yellow at the center, the abundant dark green, glossy foliage, the strong, stocky habit of growth and the large and well formed blooms which exhibit a wide range of color variation in red and yellow tones, varying with the age of bloom, temperature and soil.

No references cited.